(12) United States Patent
Johnson

(10) Patent No.: US 10,470,455 B2
(45) Date of Patent: Nov. 12, 2019

(54) FRAGRANCE AND INSECT REPELLANT DISPENSER

(71) Applicant: Charles Johnson, Pahrump, NV (US)

(72) Inventor: Charles Johnson, Pahrump, NV (US)

( * ) Notice: Subject to any disclaimer, the term of this patent is extended or adjusted under 35 U.S.C. 154(b) by 0 days.

(21) Appl. No.: 16/365,435

(22) Filed: Mar. 26, 2019

(65) Prior Publication Data

US 2019/0297870 A1 Oct. 3, 2019

Related U.S. Application Data

(60) Provisional application No. 62/650,120, filed on Mar. 29, 2018.

(51) Int. Cl.
*A01M 29/12* (2011.01)
*A61L 9/12* (2006.01)
*A01N 65/00* (2009.01)

(52) U.S. Cl.
CPC .............. *A01M 29/12* (2013.01); *A61L 9/122* (2013.01); *A01M 2200/01* (2013.01); *A01N 65/00* (2013.01)

(58) Field of Classification Search
CPC ................................ A61L 9/122; A01M 29/12
See application file for complete search history.

(56) References Cited

U.S. PATENT DOCUMENTS 4,860,726 A * 8/1989 Barker .................... A47J 36/24
126/208
5,342,584 A * 8/1994 Fritz ....................... A61L 9/122
206/807

* cited by examiner

*Primary Examiner* — Sean E Conley

(57) ABSTRACT

A fragrance and insect repellant dispenser includes a container, a lid, at least one radial set of dispensing openings, a plurality of top openings, a placement collar, a fan assembly, a power source, a plurality of locking mechanism. The radial set of dispensing openings traverses through a lateral wall of the container. The plurality of top openings traverses through a cover of the lid. The placement collar and the power source are adjacently connected onto the lid. The fan assembly is adjacently connected to the lid, opposite of the placement collar. The fan assembly is electrically connected to the power source and positioned within the container. The lid is perimetrically attached to the container by the plurality of locking mechanisms. Resultantly, the fan assembly is able to dispense at least one solution of fragrance and insect repellant through the plurality of dispensing openings and the plurality of top openings.

19 Claims, 11 Drawing Sheets

FRAGRANCE AND INSECT REPELLANT DISPENSER

The current application claims a priority to the U.S. Provisional Patent application Ser. No. 62/650,120 filed on Mar. 29, 2018.

FIELD OF THE INVENTION

The present invention generally relates to fragrance and insect repellant diffusers. More specifically, the present invention relates to solar-powered and portable diffuser which dispenses fragrances and insect repellant for long periods of time.

BACKGROUND OF THE INVENTION

Outdoor activities encompass a wide range of activities performed in diverse locations: from camping in the woods to sitting on a patio next to a campfire. While outdoor activities can be full of pleasant experiences, various aspects can reduce the enjoyment of people while performing outdoor activities. For example, insects are a known annoyance for people who perform outdoor activities. While insects are an annoyance, insects can also be dangerous as many insects can carry viruses and bacteria which can cause multiple disease on humans, such as Malaria. Other negative aspects of outdoor activities can be the odors or smells which one may experience outdoors. While many natural odors and smells can be pleasant and relaxing, pollution and other unpleasant natural smells can ruin the outdoor experience. Many products have been provided to help address these issues. Insect repellants have been provided to keep insects away from people. Insect repellants are usually provided on portable containers and dispensers which require manual operation from the user every time the user desires to dispense some insect repellant. Unfortunately, few devices allow for constant dispensing of insect repellant without user intervention. Other devices such as diffusers have been provided to dispense fragrances and other substances. However, most of these devices are often adapted for indoor use and lack a power system which allows for extended use. Thus, a portable device adapted for outdoor use which comprises a mechanism that effectively dispenses fragrances, insect repellants, and other substances in a constant, automatic fashion with few or no intervention from the user is beneficial and necessary.

An objective of the present invention is to provide a solar powered and portable diffuser which dispenses fragrances and insect repellant for long periods of time as the present invention addresses the aforementioned issues. The present invention comprises a solar-powered structure which continuously dispenses at least one solution, preferably comprising insect repellant ingredients and other relaxing mellow fragrances. Another objective of the present invention is to provide an apparatus that is easy to use and can be safely used indoors or outdoors. Another objective of the present invention is to provide a formula composition which provides a relaxing, fresh fragrance.

SUMMARY OF THE INVENTION

The present invention is a solar powered fragrances and insect repellant diffuser. The present invention comprises a solar-powered fan mechanism which continuously dispenses a first solution into the surroundings. The present invention is preferably utilized for outdoor activities and comprises a structure body that allows air flow to pass through and naturally disperse the first solution into the surroundings. The present invention further comprises a removable dispenser which continuously provides a second solution at a constant rate as the second solution is also naturally disperse into the surroundings.

DETAIL DESCRIPTIONS OF THE INVENTION

Figure 1:
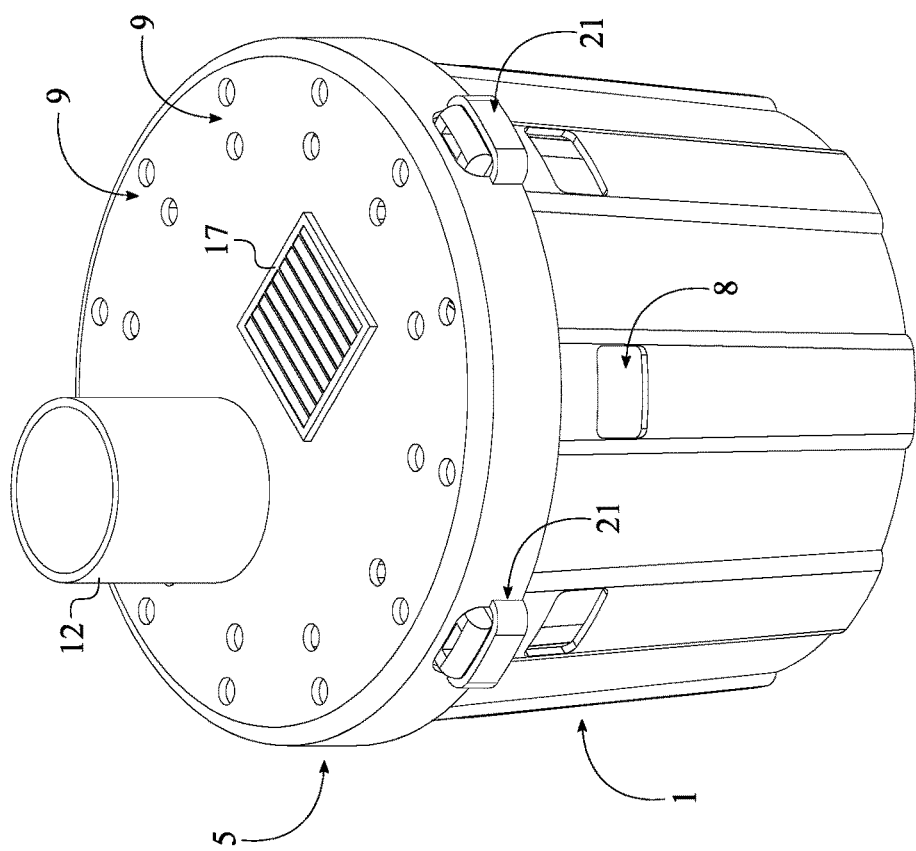
FIG. 1 is a top perspective view of the present invention.

All illustrations of the drawings are for the purpose of describing selected versions of the present invention and are not intended to limit the scope of the present invention.

The present invention is a fragrance and insect repellant dispenser that can be easily operated within an indoor environment or an outdoor environment. The present invention also naturally and efficiently dispenses fragrance and insect repellant for a longer time period without any user intervention. The present invention comprises a container 1, a lid 5, at least one radial set of dispensing openings 8, a plurality of top openings 9, a placement collar 12, a fan assembly 13, a power source 17, and a plurality of locking mechanisms 21 as shown in FIG. 1-3.

Figure 2:
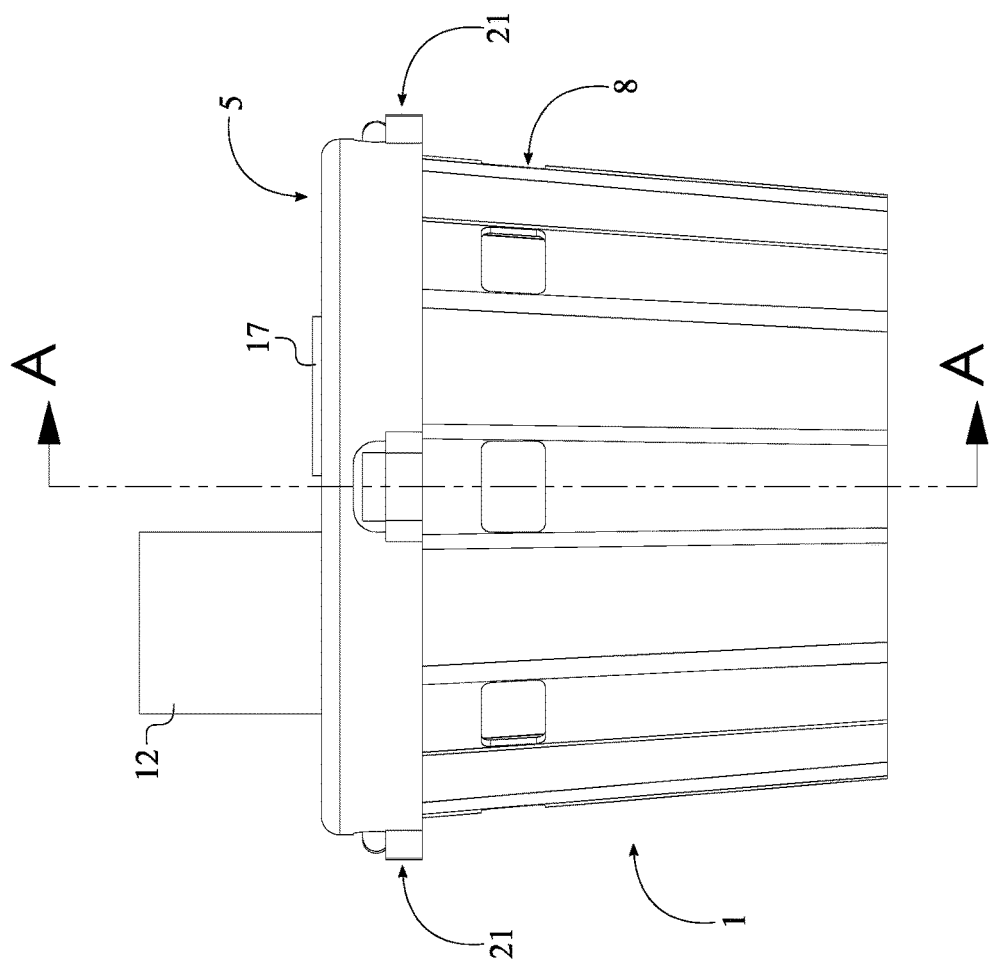
FIG. 2 is a side view of the present invention, showing the plane upon which a cross sectional view is taken shown in FIG. 3.
Figure 3:
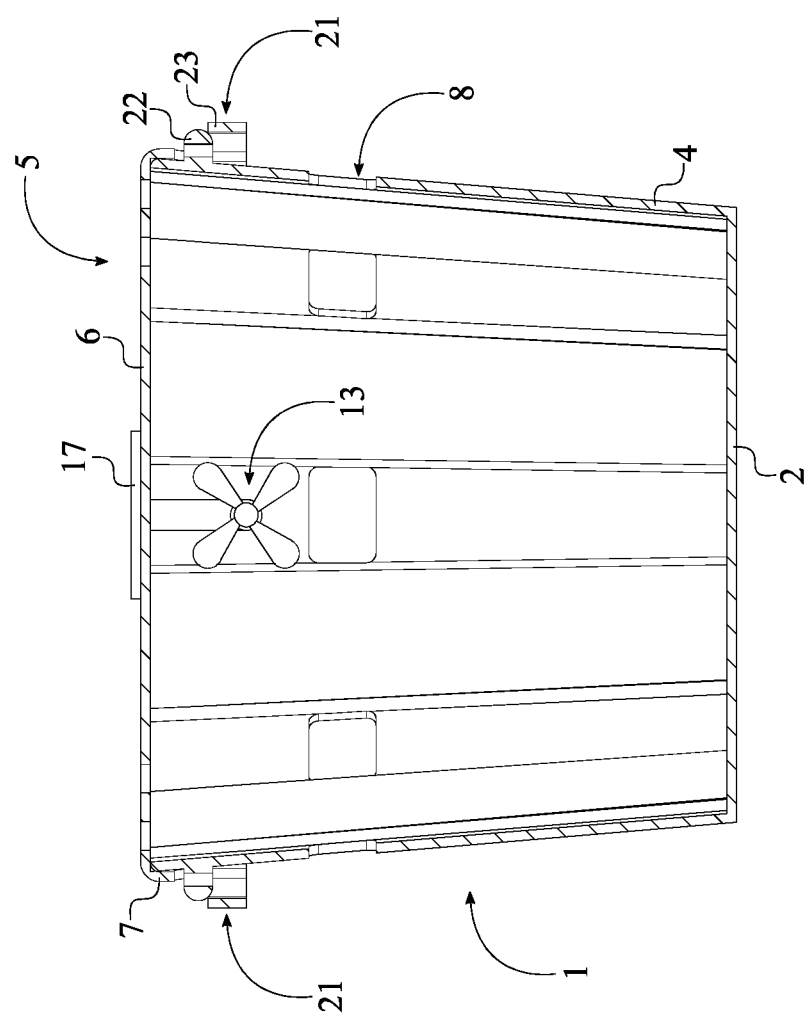
FIG. 3 is a cross section view of the present invention taken along line A-A of FIG. 2, showing the fan assembly within the container.

In reference to the general configuration of the present invention that is shown in FIG. 1-3, the lid 5 is perimetrically attached to the container 1 by the plurality of locking mechanisms 21 as a quantity of second fragrance/insect repellant is stored within the container 1 and a quantity of first fragrance/insect repellant is stored within a removable fragrance unit that engages with the placement collar 12. The quantity of first fragrance/insect repellant and the quantity of second fragrance/insect repellant are mixed and dispensed through the radial set of dispensing openings 8 and the plurality of top openings 9. The radial set of dispensing openings 8 traverses through the container 1 thus enabling the dispensing process through the container 1. The plurality of top openings 9 traverses through the lid 5 thus enabling the dispensing process through the lid 5. The fan assembly 13 that is powered through the power source 17 aids the dispensing process of the quantity of first fragrance/insect repellant and the quantity of second fragrance/insect repellant.

Figure 4:
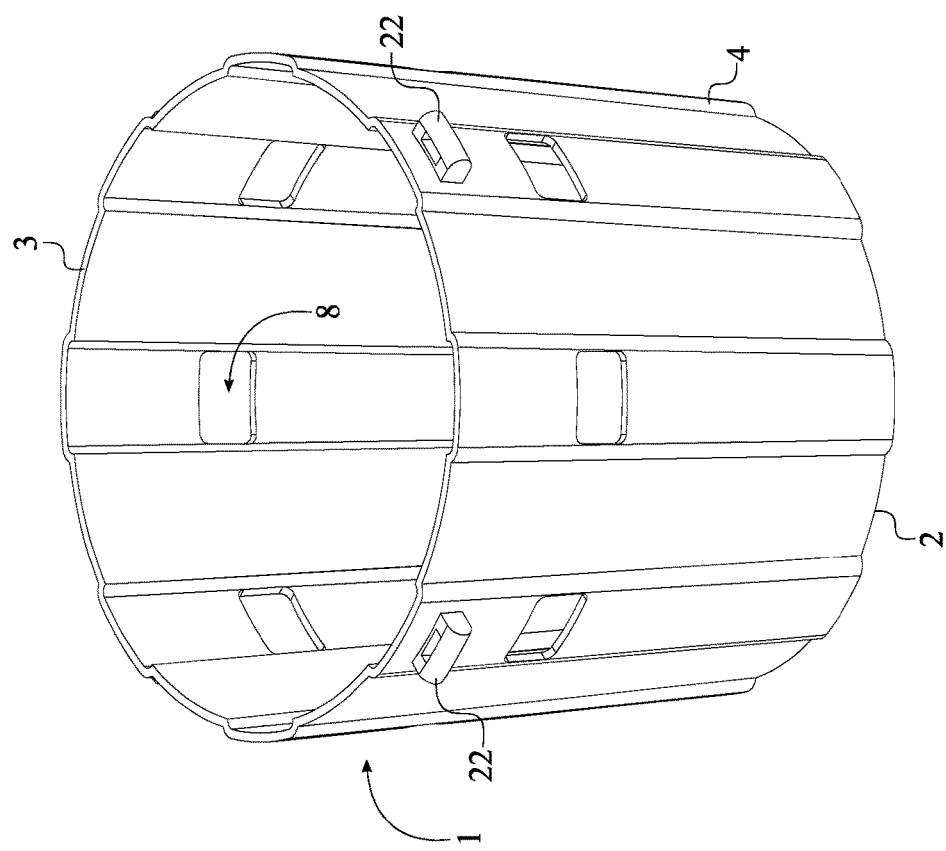
FIG. 4 is a top perspective view of the container of the present invention.
Figure 5:
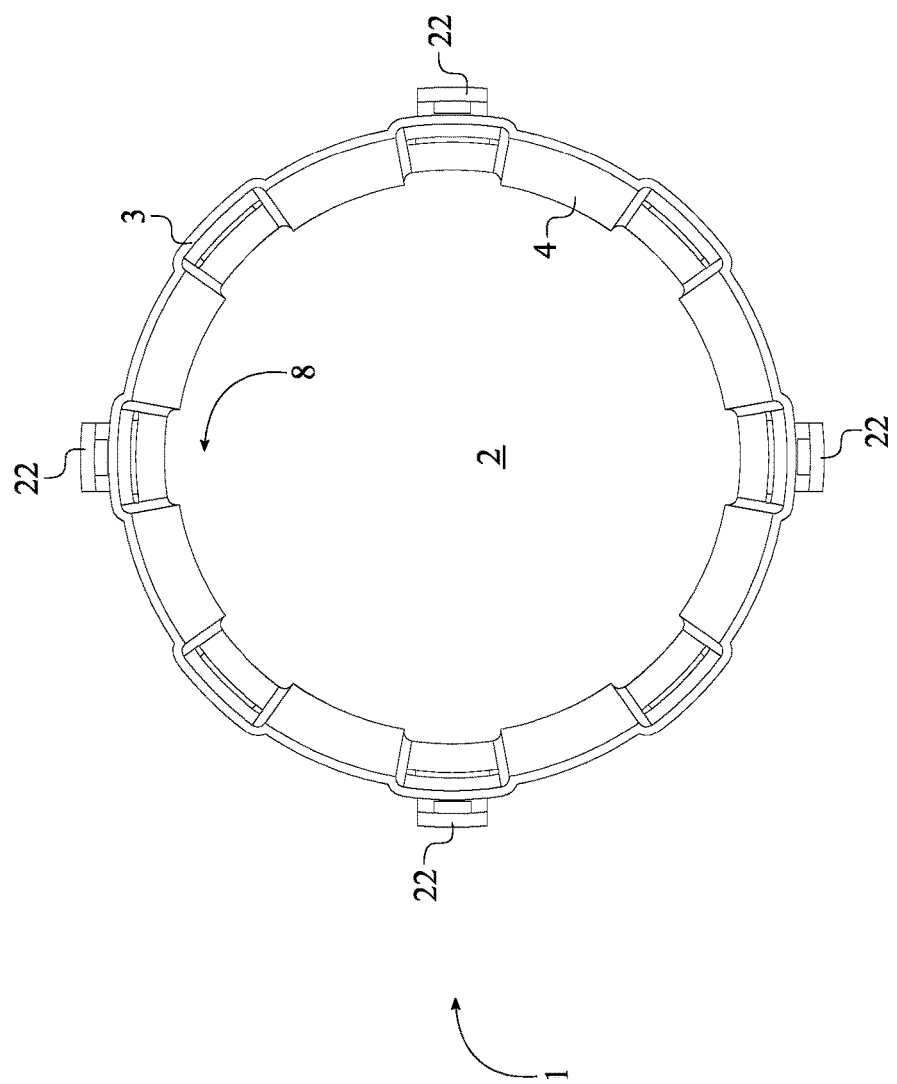
FIG. 5 is a top view of the container of the present invention.

The container 1 functions as a reservoir for the quantity of second fragrance/insect repellant before the quantity of first fragrance/insect repellant periodically drips into the container 1 through the removable fragrance unit. In reference to FIG. 4-5, the container 1 comprises a base 2, a top edge 3, and a lateral wall 4. More specifically, the lateral wall 4 is perimetrically connected around the base 2 about a bottom edge of the lateral wall 4. The top edge 3 and the base 2 are oppositely positioned of each other about the lateral wall 4 so that the volume of the container 1 can be formed within the base 2 and the lateral wall 4. The lateral wall 4 provides the height of the container 1 and a surface area so that the lid 5 can be attached. Furthermore, the radial set of dispensing openings 8 traverses through the lateral wall 4 and positioned adjacent to the top edge 3. The radial set of dispensing openings 8 is circumferentially positioned around the lateral wall 4 so that the quantity of first fragrance/insect repellant and the quantity of second fragrance/insect repellant can be equally dispensed around the present invention. In other words, the radial set of dispensing openings 8 can be arranged in a pattern along the lateral wall 4 in order to optimize the air flow into/out of the container 1 thus maximizing the dispensing process of the quantity of first fragrance/insect repellant and the quantity of second fragrance/insect repellant.

Figure 6:
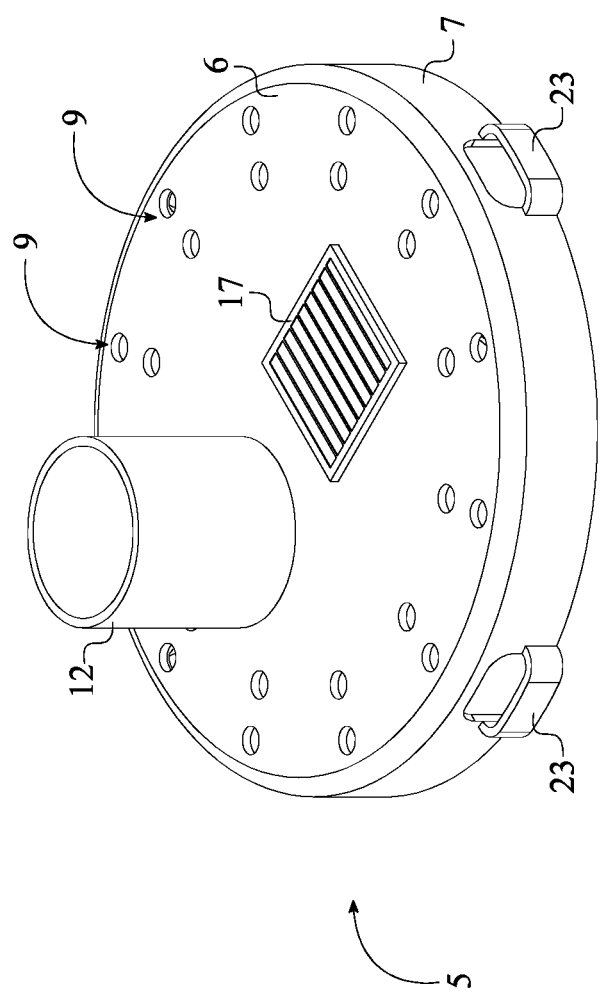
FIG. 6 is a top perspective view of the lid of the present invention, showing the placement collar and the power source.

The lid 5 encloses the container 1 from the top edge 3 and comprises a cover 6 and a flange 7. In reference to FIG. 6-7, the flange 7 is perimetrically connected around the cover 6 so that the cover 6 can be placed atop the top edge 3 and the flange 7 can be perimetrically positioned around the lateral wall 4. Furthermore, the plurality of top openings 9 traverses through the cover 6 so that the quantity of first fragrance/insect repellant and the quantity of second fragrance/insect repellant can be equally dispensed through the cover 6.

Figure 8:
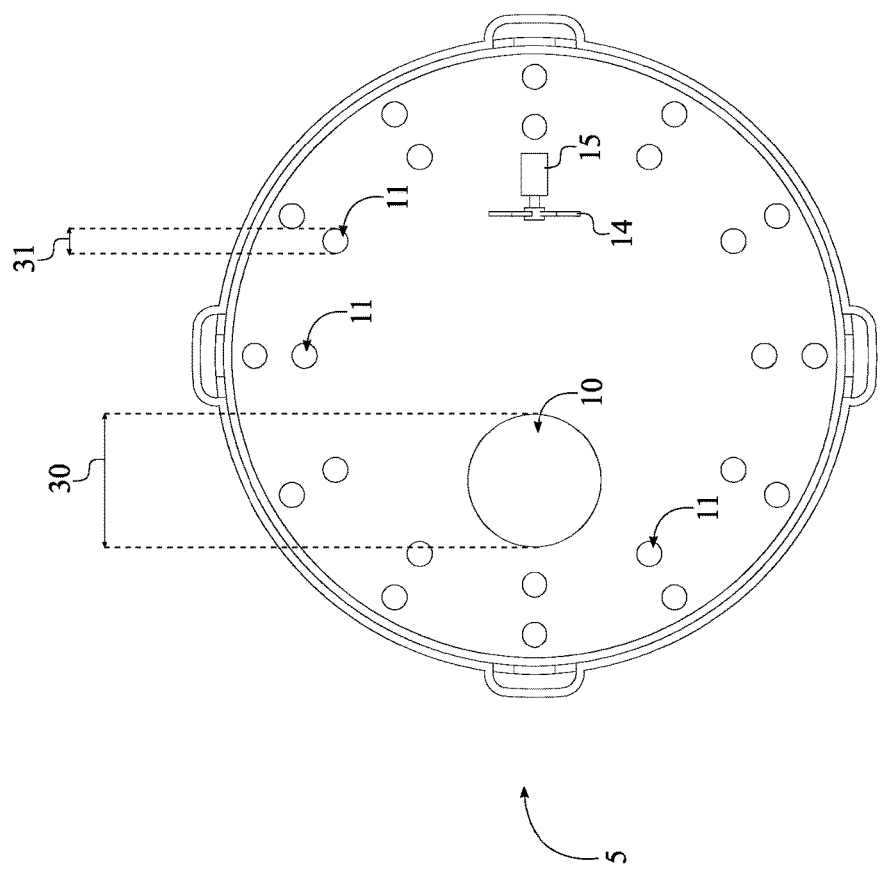
FIG. 8 is a bottom view of the lid of the present invention showing the diameter difference between each top dispensing openings and the main opening.
Figure 9:
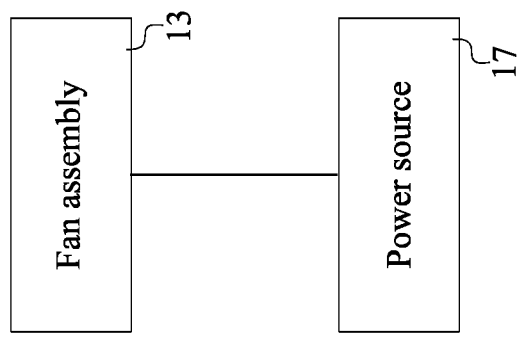
FIG. 9 is a schematic view showing the electrical connection between the fan assembly and the power source.
Figure 10:
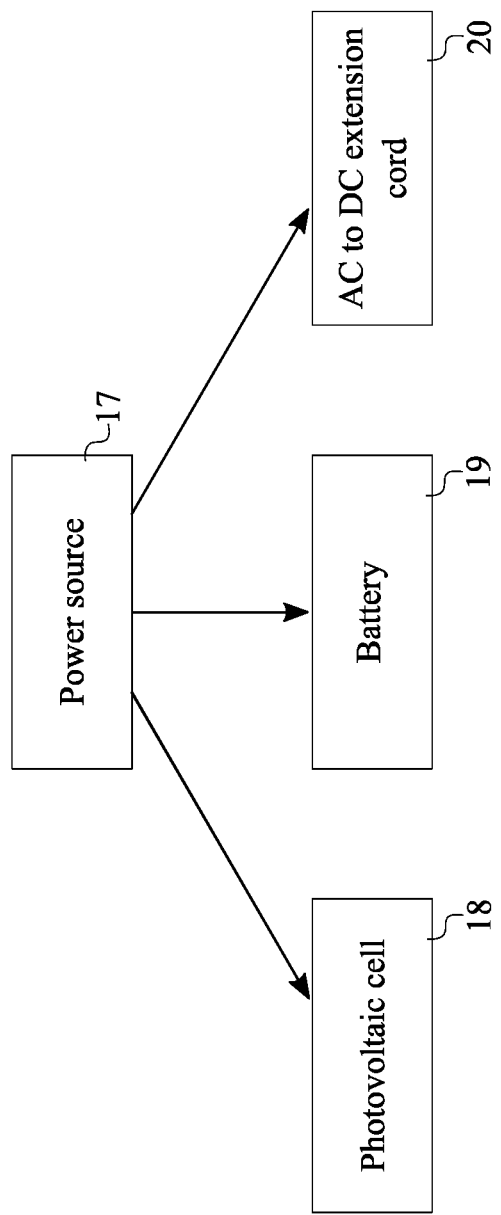
FIG. 10 is a schematic view showing the different types of the power source.

The plurality of top openings 9 traverses through the cover 6 and comprises a main opening 10 and a plurality of top dispensing openings 11 as shown in FIG. 8. The main opening 10 traverses through the cover 6 and functions as an inlet for the quantity of first fragrance/insect repellant so that the quantity of first fragrance/insect repellant can be dispensed into the container 1 from the removable fragrance unit. The plurality of dispensing top openings 9 traverses through the cover 6 and functions as outlets so that the quantity of first fragrance/insect repellant and the quantity of second fragrance/insect repellant can be dispensed out of the container 1. As a result, the radial set of dispensing openings 8 and the plurality of top dispensing openings 11 are able to equally and efficiently dispense the quantity of first fragrance/insect repellant and the quantity of second fragrance/insect repellant around the present invention.

Figure 7:
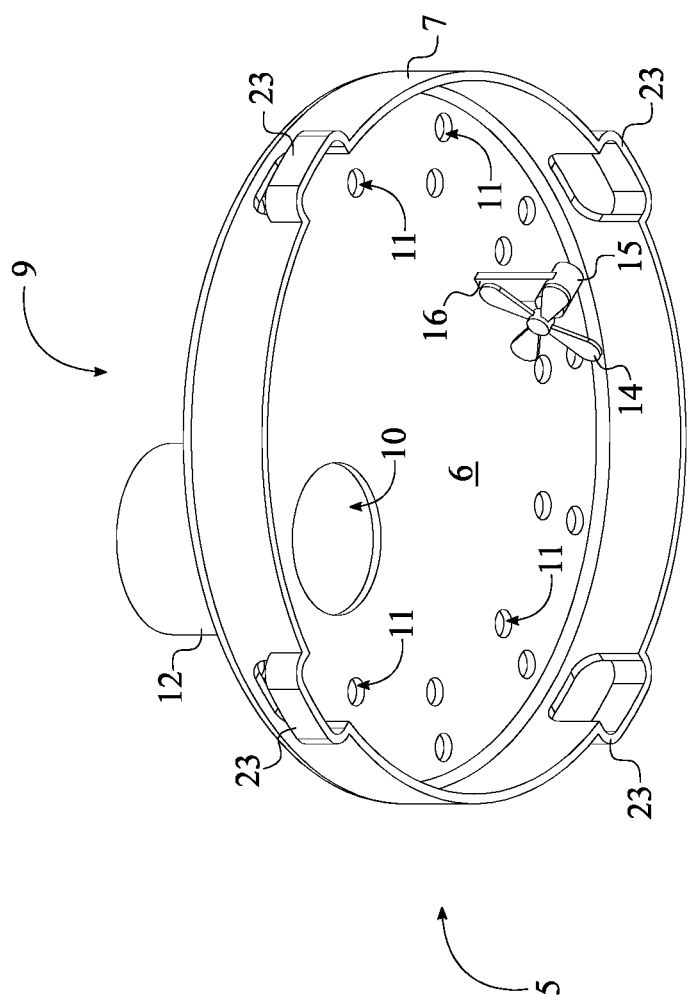
FIG. 7 is a bottom perspective view of the lid of the present invention, showing the fan assembly, the plurality of top dispensing openings, and the main opening.
Figure 11:
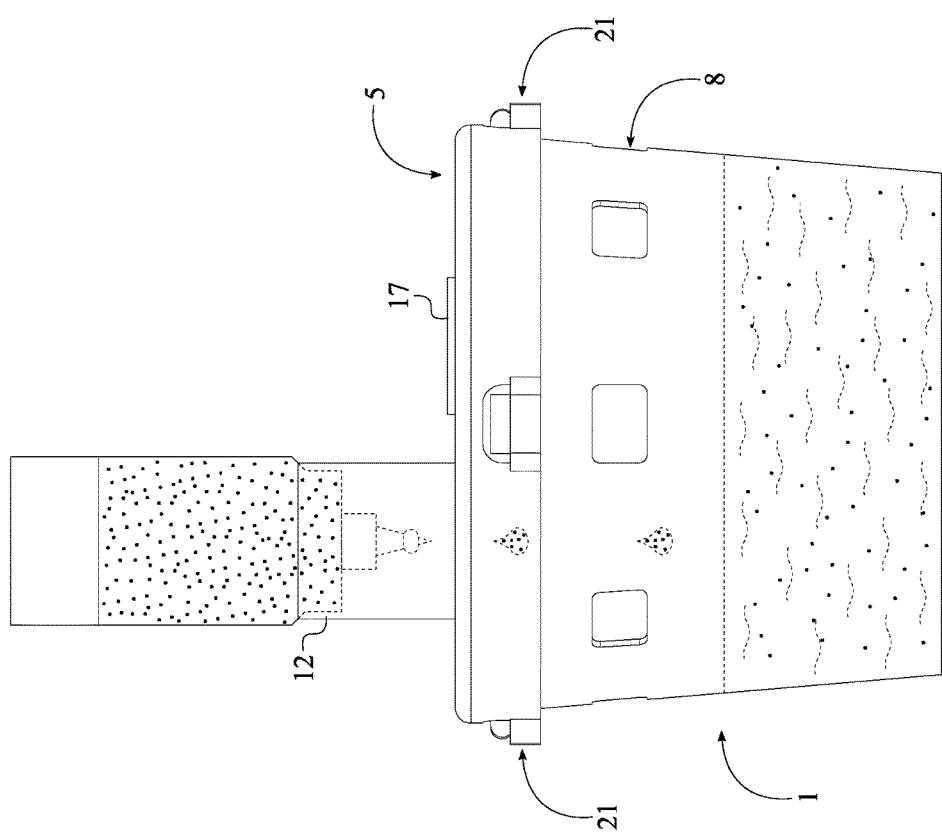
FIG. 11 is a schematic view showing the dripping and mixing process of the quantity of first fragrance/insect repellant into the quantity of second fragrance/insect repellant.

The placement collar 12 that functions as a seat for the removable fragrance unit and concentrically positions with the main opening 10 as shown in FIG. 7. More specifically, the removable fragrance unit contains the quantity of first fragrance/insect repellant before the quantity of first fragrance/insect repellant periodically drips into the container 1 and is able to discharges the quantity of first fragrance/insect repellant through the main opening 10 as shown in FIG. 11. Furthermore, a diameter 30 of the main opening 10 is larger than a diameter 31 of each top dispensing openings 11 so that the lid 5 is able to accommodate a larger sized removable fragrance unit. Furthermore, a fastening mechanism can be internally integrated into the placement collar 12 and the removable fragrance unit so that the removable fragrance unit can be attached the lid 5. For example, the fastening mechanism can be a male tread fastener and a female tread fastener as the removable fragrance unit is threadedly screwed into the placement collar 12.

In order to periodically discharge the quantity of first fragrance/insect repellant, the removable fragrance unit comprises a bottle, a spout, and a drip tip. The spout is terminally connected to the bottle so that the stored quantity of first fragrance/insect repellant within the bottle can be discharged through the spout. The drip tip is terminally attached to the spout and positioned opposite of the bottle. The drip tip enables the periodic dripping of the quantity of first fragrance/insect repellant. Furthermore, the drip tip can also be adjusted to extend or shorten the interval between each drip of the quantity of first fragrance/insect repellant.

The fan assembly 13 radially expands the coverage area for the quantity of first fragrance/insect repellant and the quantity of second fragrance/insect repellant within the present invention. More specifically, the fan assembly 13 is adjacently connected to the lid 5. The fan assembly 13 is oppositely positioned to the placement collar 12 and the power source 17 about the lid 5, wherein the fan assembly 13 is positioned within the container 1. In reference to FIG. 6 and FIG. 9, the power source 17 is adjacently connected onto the lid 5 and electrically connected to the fan assembly 13. In reference to FIG. 7-8, the fan assembly 13 comprises a rotor 14, a stator 15, and a bracket 16. The rotor 14, which is the rotating component unit of the fan assembly 13, is axially connected within the stator 15. The stator 15 is the stationary component units of the fan assembly 13 and is connected to the lid 5 by the bracket 16. As a result, the fan assembly 13 is able to function similar to traditional fan thus assisting the dispensing process of the quantity of first fragrance/insect repellant and the quantity of second fragrance/insect repellant.

In reference to FIG. 10, the power source 17 of the present invention is preferably at least one photovoltaic cell 18 so that the present invention does not require user intervention to operate. Furthermore, the photovoltaic cell 18 is able to power the fan assembly 13 in indoor and outdoor environments. In a first alternative embodiment of the present invention, the power source 17 can be a battery 19 that is sufficient enough to operate the fan assembly 13 wherein the battery 19 can be a primary battery or a secondary battery. In a second alternative embodiment of the present invention, the power source 17 can be an alternating-current (AC) to direct-current (DC) extension cord 20. More specifically, the AC to DC extension cord 20 is plugged into an external power outlet so that the AC can be converted into DC that operates the fan assembly 13. Optionally, the second alternative embodiment can also comprise an on/off switch that is electrically connected to the AC to DC extension cord 20 so that the fan assembly 13 can selectively turn-on and turn-off.

The plurality of locking mechanisms 21 that attaches the lid 5 to the container 1 each comprises a first locking section 22 and a second locking section 23. The first locking section 22 is integrated to the lateral wall 4. The second locking section 23 is integrated to the flange 7. Resultantly, the first locking section 22 and the second locking section 23 are engaged to each other thus attaching the lid 5 and container 1 to each other. The present invention preferably utilizes a male and female snap-fasteners as the plurality of locking mechanism 21. However, the present invention is not limited to the abovementioned locking mechanism 21 and can be any other type of easily detachable locking mechanisms such as latch fasteners, hook-and-loop fasteners, screw fasteners, tongue and grove fasteners, and friction fasteners.

The quantity of first fragrance/insect repellant is in fluid stage and preferably comprises Cetrimonium Chloride, Lemon Grass, Citronella, Sodium Pyroglutamic Acid (PCA), Aloe Vera Barbadensis, Lavender, Rosemary, Scotch Pine, Mint, Cloves, Apple Cider Vinegar, Mum, Marigold, and a plurality of inert liquid ingredients. The quantity of second fragrance/insect repellant is initially in solid stage and preferably comprises a plurality of products from milling including, but not limited to, pine needles, Mum, Lemon Grass, etc. In order to properly be utilized within the present invention, the quantity of second fragrance/insect repellant is dissolve in water so that the quantity of second fragrance/insect repellant can be stored within the container 1.

Although the invention has been explained in relation to its preferred embodiment, it is to be understood that many other possible modifications and variations can be made without departing from the spirit and scope of the invention as hereinafter claimed.

What is claimed is:

1. A fragrance and insect repellant dispenser comprises:
   a container;
   a lid;
   at least one radial set of dispensing openings;
   a plurality of top openings;
   a placement collar;
   a fan assembly;
   a power source;
   a plurality of locking mechanisms;
   the radial set of dispensing openings traversing through the container;
   the plurality of top openings traversing through the lid;
   the placement collar being adjacently connected onto the lid;
   the power source being adjacently connected onto the lid;
   the fan assembly being adjacently connected to the lid;
   the fan assembly being electrically connected to the power source;
   the fan assembly being oppositely positioned to the placement collar and the power source about the lid;
   the fan assembly being positioned within the container; and
   the lid being perimetrically attached to the container by the plurality of locking mechanisms.

2. The fragrance and insect repellant dispenser as claimed in claim 1 comprises:
   the container comprises a base, a top edge, and a lateral wall;
   the lateral wall being perimetrically connected around the base, wherein the container receives a quantity of second fragrance/insect repellant;
   the top edge and the base being oppositely positioned of each other about the lateral wall; and
   the radial set of dispensing openings traversing through the lateral wall, adjacent to the top edge.

3. The fragrance and insect repellant dispenser as claimed in claim 1 comprises:
   the lid comprises a cover and a flange;
   the flange being perimetrically connected around the cover; and
   the plurality of top openings traversing through the cover.

4. The fragrance and insect repellant dispenser as claimed in claim 1 comprises:
   the plurality of top openings comprises a main opening and a plurality of top dispensing openings;
   the main opening traversing through a cover of the lid;
   the plurality of top dispensing openings traversing through the cover of the lid; and
   the placement collar being concentrically positioned to the main opening, wherein the placement collar receives a removable fragrance unit.

5. The fragrance and insect repellant dispenser as claimed in claim 4, wherein a diameter of the main opening is larger than a diameter of each top dispensing openings.

6. The fragrance and insect repellant dispenser as claimed in claim 1 comprises:
   the fan assembly comprises a rotor, a stator, and a bracket;
   the rotor being axially connected within the stator; and
   the stator being connected to the lid by the bracket.

7. The fragrance and insect repellant dispenser as claimed in claim 1, wherein the power source is at least one photovoltaic cell.

8. The fragrance and insect repellant dispenser as claimed in claim 1, wherein the power source is a battery.

9. The fragrance and insect repellant dispenser as claimed in claim 1, wherein the power source is an alternating-current to direct-current extension cord.

10. The fragrance and insect repellant dispenser as claimed in claim 1 comprises:
    the plurality of locking mechanisms each comprises a first locking section and a second locking section;
    the first locking section being integrated to a lateral wall of the container;
    the second locking section being integrated to a flange of the lid; and
    the first locking section and the second locking section being engaged to each other.

11. A fragrance and insect repellant dispenser comprises:
    a container;
    a lid;
    at least one radial set of dispensing openings;
    a plurality of top openings;
    a placement collar;
    a fan assembly;
    a power source;
    a plurality of locking mechanisms;
    the plurality of top openings comprises a main opening and a plurality of top dispensing openings;
    the radial set of dispensing openings traversing through the container;
    the plurality of top openings traversing through the lid;
    the main opening traversing through a cover of the lid;
    the plurality of top dispensing openings traversing through the cover of the lid;
    the placement collar being adjacently connected onto the lid;
    the placement collar being concentrically positioned to the main opening, wherein the placement collar receives a removable fragrance unit;
    the power source being adjacently connected onto the lid;
    the fan assembly being adjacently connected to the lid;
    the fan assembly being electrically connected to the power source;
    the fan assembly being oppositely positioned to the placement collar and the power source about the lid;
    the fan assembly being positioned within the container; and
    the lid being perimetrically attached to the container by the plurality of locking mechanisms.

12. The fragrance and insect repellant dispenser as claimed in claim 11 comprises:

the container comprises a base, a top edge, and a lateral wall;

the lateral wall being perimetrically connected around the base, wherein the container receives a quantity of second fragrance/insect repellant;

the top edge and the base being oppositely positioned of each other about the lateral wall; and the radial set of dispenser openings traversing through the lateral wall, adjacent to the top edge.

13. The fragrance and insect repellant dispenser as claimed in claim 11 comprises:

the lid further comprises a flange;

the flange being perimetrically connected around the cover; and the plurality of top openings traversing through the cover.

14. The fragrance and insect repellant dispenser as claimed in claim 11, wherein a diameter of the main opening is larger than a diameter of each top dispensing openings.

15. The fragrance and insect repellant dispenser as claimed in claim 11 comprises:

the fan assembly comprises a rotor, a stator, and a bracket;

the rotor being axially connected within the stator; and the stator being connected to the lid by the bracket.

16. The fragrance and insect repellant dispenser as claimed in claim 11, wherein the power source is at least one photovoltaic cell.

17. The fragrance and insect repellant dispenser as claimed in claim 11, wherein the power source is a battery.

18. The fragrance and insect repellant dispenser as claimed in claim 11, wherein the power source is an alternative-current to direct-current extension cord.

19. The fragrance and insect repellant dispenser as claimed in claim 11 comprises:

the plurality of locking mechanisms each comprises a first locking section and a second locking section;

the first locking section being integrated to a lateral wall of the container;

the second locking section being integrated to a flange of the lid; and the first locking section and the second locking section being engaged to each other.

* * * * *